(12) United States Patent
Lunak et al.

(10) Patent No.: US 7,052,465 B1
(45) Date of Patent: May 30, 2006

(54) NONINVASIVE BLOOD PRESSURE MONITOR HAVING AUTOMATIC HIGH MOTION TOLERANCE

(75) Inventors: Donna R. Lunak, Saint Paul, MN (US); Robert S. Bryngelson, Saint Paul, MN (US)

(73) Assignee: Medwave, Inc., Danvers, MA (US)

( * ) Notice: Subject to any disclaimer, the term of this patent is extended or adjusted under 35 U.S.C. 154(b) by 0 days.

(21) Appl. No.: 11/121,305

(22) Filed: May 2, 2005

(51) Int. Cl.
*A61B 5/02* (2006.01)
(52) U.S. Cl. ..................... 600/485; 600/490
(58) Field of Classification Search ............... 600/490
See application file for complete search history.

(56) References Cited

U.S. PATENT DOCUMENTS

| | | | |
|---|---|---|---|
| 3,444,856 A * | 5/1969 | Settler et al. ............... 600/493 |
| 5,450,852 A | 9/1995 | Archibald et al. |
| 5,640,964 A | 6/1997 | Archibald et al. |
| 5,642,733 A | 7/1997 | Archibald et al. |
| 5,649,542 A * | 7/1997 | Archibald et al. .......... 600/485 |
| 5,720,292 A | 2/1998 | Poliac |
| 5,722,414 A | 3/1998 | Archibald et al. |
| 5,738,103 A | 4/1998 | Poliac |
| 5,797,850 A | 8/1998 | Archibald et al. |
| 5,941,828 A | 8/1999 | Archibald et al. |
| 6,132,382 A | 10/2000 | Archibald et al. |
| 6,159,157 A | 12/2000 | Archibald et al. |
| 6,241,679 B1 | 6/2001 | Curran |
| 6,245,022 B1 | 6/2001 | Archibald et al. |
| 6,413,224 B1 * | 7/2002 | Ogura et al. ............... 600/493 |
| 6,558,335 B1 | 5/2003 | Thede |
| 6,589,185 B1 | 7/2003 | Archibald et al. |
| 6,695,789 B1 | 2/2004 | Thede et al. |
| 6,699,199 B1 * | 3/2004 | Asada et al. ............... 600/504 |
| 6,730,040 B1 * | 5/2004 | Lee et al. ................... 600/485 |

OTHER PUBLICATIONS

Freescale Semiconductor, Inc., Technical Data for High Volume Pressure Sensor For Disposable Applications, Types MPX2300DT1 and MPX2301DT1, 2004, 4 pages.

(Continued)

*Primary Examiner*—Max F. Hindenburg
*Assistant Examiner*—Patricia C Mallari
(74) *Attorney, Agent, or Firm*—Altera Law Group, LLC

(57) ABSTRACT

The noninvasive measurement of a patient's blood pressure is achieved automatically in high motion situations by using a dual signal channel pressure sensor in a method and system that acquires pressure waveform data while the degree of compression of an artery is being varied. Two pressure measurement channels are used, one being a main channel for monitoring pressure in the pressure transmission path, and the other being a reference channel for monitoring pressure in a wall through which a holddown force is applied. A caregiver applies the NIBP sensor to the patient. Immediately before the patient is about to engage in high motion activities or be placed in a high motion environment, the caregiver turns ON the automatic HMT function, and proceeds with his or her duties while observing the patient to ensure that the patient is quiet until the NIBP monitor acquires a certain number of waveforms without resetting. Once this has occurred, the caregiver may permit the high motion activity to begin. The automatic high motion tolerance algorithm reduces the adverse effects of high motion artifacts from the main channel using the main channel and reference channel signals.

4 Claims, 10 Drawing Sheets

OTHER PUBLICATIONS

Medwave, Inc., MEDWAVE, Inc. High Motion Tolerant Software for Vasotrac® Debuts at NASPE May 15, 2001, 1 page (Retrieved from the Internet URL: http://www.medwave.com/5_15_01.html on Apr. 18, 2005).

Medwave, Inc. NIMP and EMS, 1 page (Retrieved from the Internet URL: http://www.medwave.com on Apr. 28, 2005).

Medwave, Inc., Prehospital Emergency Care Publishes Study Showing Effectiveness of Medwave's Technology in Emergency Transport. 1 page, Feb. 9, 2005 (Retrieved from the Internet URL: http://www.vasotrac,com/2_9_05.html on Apr. 28, 2005).

Medwave, Inc., Study Showing Effectiveness of Vasotrac in Out of Hospital (Transport) Setting Accepted for Presentation at Annual SAEM Meeting in Orlando Feb. 25, 2004, 1 page (Retrieved from the Internet URL: http://www.vasotrac.com/2_25_04.html on Apr. 28, 2005).

Medwave, Inc., Vasotrac® APM 205A FAQ Frequently Asked Questions, 3 pages, copyrught 2001 (Retrieved from the Internet URL: http://mdwv.com/TRACFAQ.HTM on Dec. 28, 2002).

Medwave, Inc., Vasotrac® APM 205A Technical Information System Features and Specifications, 3 pages, copyright 2001 (Retrieved from the Internet URL: http://www.mdwv.com/TRACTECH.HTM on Dec. 28, 2002).

Medwave, Inc., Vasotrac® Model APM 205A Non-Invasive Blood Pressure Monitor Operator's Manual, Rev. K, May 2004, 51 pages.

Medwave, Inc., Vasotrac® Monitor Brochure, Feb. 21, 2001, 12 pages.

PACT, Adaptive Filter Based on the LMS-Algorithm, 12 pages (date unknown but prior to filing date).

U.S. Appl. No. 11/072,199 for Kevin R. Evans entitled "Articulated Placement Guide For Sensor-Based Noninvasive Blood Pressure Monitor", filed Mar, 4, 2005.

U.S. Appl. No. 11/072,916 for Kevin R. Evans entitled "Sensor-Based Apparatus and Method For Portable Noninvasive Monitoring of Blood Pressure", filed Mar, 4, 2005.

Medwave, Inc., Vasotrac® Model APM205A Non-Invasive Blood Pressure Monitor Operator's Manual, Rev. L, Dec. 2004, 54 pages.

* cited by examiner

NONINVASIVE BLOOD PRESSURE MONITOR HAVING AUTOMATIC HIGH MOTION TOLERANCE

BACKGROUND OF THE INVENTION

1. Field of the Invention

The present invention relates to the noninvasive monitoring of arterial blood pressure, and more particularly to the noninvasive monitoring of arterial blood pressure, including systolic pressure, diastolic pressure, mean pressure, pulse rate, and pressure waveform characteristics, under high motion conditions.

2. Description of the Related Art

Various different methods may be used to measure blood pressure: invasive, oscillometric, auscultatory, tonometric, and sensor-based. The invasive method, which is known as an arterial line (A-Line), involves insertion of a needle into the artery and is generally accepted as the "gold standard." The other methods are noninvasive. The oscillometric method determines blood pressure from the amplitude of pressure oscillations in a pressurized cuff, typically measured within the cuff while the cuff is slowly deflated. The auscultatory method involves monitoring Korotkoff sounds as an inflated cuff placed around a cooperating artery of the patient slowly deflates. Systolic pressure is indicated when Korotkoff sounds begin to occur, while diastolic pressure is indicated when the Korotkoff sounds become muffled or disappear. The tonometric method typically uses an array of pressure sensitive elements which have at least one dimension smaller than the lumen of the underlying artery in which blood pressure is to be measured. The array is pressed against the site to measure a reference pressure directly from the wrist, which is correlated with arterial pressure.

The oscillometric, auscultatory, and tonometric methods have not been entirely satisfactory. Because both the oscillometric and the auscultatory methods require inflation of a cuff, they are not entirely suitable for performing frequent measurements and measurements over long periods of time. The frequency of measurement is limited by the time required to inflate and deflate the cuff, and the pressure imposed by the cuff is uncomfortable to the patient. Moreover, both the oscillometric and auscultatory methods lack accuracy and consistency. While the tonometric method eliminates the need for a cuff, accurately positioning and maintaining the individual pressure sensitive elements over the underlying artery is difficult. The tonometric method requires that the system be calibrated to compensate for gain, which is the ratio of pressure outside the artery to the pressure inside the artery. Improper placement will make calibration ineffective, and patient movement during measurement will change the gain and affect the accuracy of the measurement.

Various sensor-based noninvasive blood pressure ("NIBP") monitoring approaches that overcome the disadvantages of the invasive, oscillometric, auscultatory and tonometric methods have been developed by Medwave, Inc. of Danvers, Mass. Some of these approaches are described in the following United States patents: U.S. Pat. No. 5,450,852 entitled "Continuous Non-Invasive Blood Pressure Monitoring System" which issued Sep. 19, 1995 to Archibald et al.; U.S. Pat. No. 5,640,964 entitled "Wrist Mounted Blood Pressure Sensor" which issued Jun. 24, 1997 to Archibald et al.; U.S. Pat. No. 5,642,733 entitled "Blood Pressure Sensor Locator" which issued Jul. 1, 1997 to Archibald et al.; U.S. Pat. No. 5,649,542 entitled "Continuous Non-Invasive Blood Pressure Monitoring System" which issued Jul. 22, 1997 to Archibald et al.; U.S. Pat. No. 5,720,292 entitled "Beat Onset Detector" which issued Feb. 24, 1998 to Poliac; U.S. Pat. No. 5,722,414 entitled "Continuous Non-Invasive Blood Pressure Monitoring System" which issued Mar. 3, 1998 to Archibald et al.; U.S. Pat. No. 5,738,103 entitled "Segmented Estimation Method" which issued Apr. 14, 1998 to Poliac; U.S. Pat. No. 5,797,850 entitled "Method and Apparatus for Calculating Blood Pressure of an Artery" which issued Aug. 25, 1998 to Archibald et al.; U.S. Pat. No. 5,941,828 entitled "Hand-Held Non-Invasive Blood Pressure Measurement Device" which issued Aug. 24, 1999 to Archibald et al.; U.S. Pat. No. 6,159,157 entitled "Blood Pressure Measurement Device with Sensor Locator" which issued Dec. 12, 2000 to Archibald et al.; U.S. Pat. No. 6,241,679 entitled "Non-Invasive Blood Pressure Sensing Device and Method using Transducer with Associate Memory" which issued Jun. 5, 2001 to Curran; U.S. Pat. No. 6,558,335 entitled "Wrist-Mounted Blood Pressure Measurement Device" which issued May 6, 2003, to Thede; U.S. Pat. No. 6,589,185 entitled "Method and Apparatus for Calculating Blood Pressure of an Artery" which issued Jul. 8, 2003, to Archibald et al.; and U.S. Pat. No. 6,695,789 entitled "Disposable Non-Invasive Blood Pressure Sensor" which issued Feb. 24, 2004, to Thede et al. As described in these patents, blood pressure is measured from pressure waveform data that is acquired non-invasively while the degree of compression of an artery is being varied. A sensor has a contact surface that includes a terminus of a pressure transmission path and a terminus of a conformable wall. The compressible wall is located adjacent to and ideally surrounds the pressure transmission path, which is effectively isolated from forces within the conformable wall. The contact surface of the sensor is positioned on the surface of an anatomical structure over the artery and a varying pressure is applied. Suitable anatomical structures include the wrist, the inside elbow, the ankle, and the top of the foot. Pressure waveforms that result from arterial blood pressure and the varying holddown pressure propagate through the pressure transmission path and are sensed by a transducer to produce pressure waveform data. The pressure waveform data is analyzed to determine waveform parameters which relate to the shape of the sensed pressure waveforms, and one or more blood pressure values are derived based upon the waveform parameters. The wall applies pressure to the artery while at the same time suppressing force in a direction generally parallel to the artery from being applied to the pressure transmission path.

While blood pressure measurements typically are made under quiescent conditions, there are circumstances under which pressure measurements must be made under high motion conditions. The high motion conditions may be imposed by external events, such as motion during emergency patient gurney or ambulance transport, or by the patient as when the patient is talking, eating, walking, or running on a treadmill. Regardless of the source, the high motion conditions may cause pressure fluctuations that are unrelated to either the blood pressure or the holddown pressure, which in turn may result in erroneous blood pressure determinations by the sensor-based type of NIBP monitor.

Various techniques have been used to compensate the blood pressure measurement for the high motion artifacts. U.S. Pat. No. 6,132,382 entitled Non-Invasive Blood Pressure Sensor with Motion Artifact Reduction which issued Oct. 17, 2000 to Archibald et al., and U.S. Pat. No. 6,245,022 entitled Non-Invasive Blood Pressure Sensor with Motion Artifact Reduction and Constant Gain Adjustment During Pressure Pulses which issued Jun. 12, 2001 to Archibald et al., describe various techniques for providing noninvasive blood pressure monitors achieving high motion tolerance. As described in the '022 patent, for example, the effects of motion artifacts on a main source signal are reduced by the use of signals from both the main source as well as from a ring source. The main signal source is sensitive to arterial pressure, although it is also somewhat sensitive to holddown pressure. The ring signal source is mainly sensitive to holddown pressure. Both signal sources are sensitive to motion artifacts. Part of the analysis of the waveform data includes the use of an adjusted gain that is substantially constant during pressure pulses, but that may vary from pulse to pulse. Signal values obtained from the ring source are multiplied by the adjusted gain.

The effectiveness of high motion tolerance has been proven in various products, including the Vasotrac® model AMP205A (Revision K) NIBP monitor with manual high motion tolerance, which was available from Medwave Inc. of Danvers, Mass. This Vasotrac NIBP monitor incorporated a High Motion Tolerance ("HMT") function that used an adaptive noise canceling ("ANC") algorithm on high-pass filtered signals from the main source and the ring source. The high pass filters generally correct small movements which may occur from slow treadmill walking speeds, ambulance and ambulatory environments, and post-operative embodiments. The ANC algorithm relies on the main-to-ring noise correlation to correct large noise levels which may occur from fast walking or running on a treadmill.

To use the HMT function on this Vasotrac NIBP monitor, monitoring is begun with HMT off. The patient is observed for at least five readings to ensure that the patient has been quiet before activating the HMT function. When HMT:ON is selected, the HMT algorithm uses the last presumably valid sweep in the prior series as a baseline. When monitoring with HMT:ON, the monitor Cycle mode should be set to "Continual." While the HMT technique provides accurate readings when the patient is moving or being moved, and while the caregiver can perform various required activities while observing the patient for high motion, the requirement on the caregiver to interrupt his or her activities in order to select HMT:ON after a given number of readings can be inconvenient to caregivers under some circumstances.

What is desired is an improved HMT function that does not require the caregiver to interrupt his or her activities, where those activities are compatible with patient observation.

BRIEF SUMMARY OF THE INVENTION

The present invention provides for greater convenience in the noninvasive sensor-based detection and measurement of arterial blood pressure under high motion conditions, without sacrificing accuracy.

These and other advantages are realized in varying degrees by the various embodiments of the present invention. One embodiment of the present invention is a method for monitoring blood pressure of a patient under high motion conditions. The method comprises securing a sensor assembly to a monitoring site on an anatomical structure of the patient from which noninvasive monitoring of blood pressure may be performed, the sensor assembly having a sensor with a main pressure channel and a reference pressure channel; applying the sensor to the monitoring site with a varying holddown force over a plurality of sequential cycles comprising an initial sequence of a predetermined number of cycles and a subsequent sequence; attempting to maintain low motion conditions over the initial sequence of the applying step; acquiring main waveform data from the main pressure channel and reference waveform data from the reference pressure channel during the applying step; monitoring at least one of the main waveform data and the reference waveform data to detect a fault in the initial sequence of the applying step; monitoring a user-activated restart control to detect a restart signal during the initial sequence of the applying step; and when no fault is detected in the waveform data monitoring step, and when no restart signal is detected in the reset control monitoring step, calculating blood pressure from the main and reference waveform data acquired in the subsequent sequence of the applying step and from at least one cycle of the initial sequence after filtration thereof with respective high pass filters, an adaptive noise canceller, and an adaptive linear predictor.

DETAILED DESCRIPTION OF THE INVENTION, INCLUDING THE BEST MODE

The noninvasive measurement of a patient's blood pressure is achieved automatically in high motion situations by using a dual signal channel pressure sensor in a method and system that acquires pressure waveform data while the degree of compression of an artery is being varied. A sensor has a contact surface that includes a terminus of a pressure transmission path next to a terminus of a compressible body. The compressible body preferably is an encircling wall that is located adjacent to and surrounds the pressure transmission path and includes a conformable section, and the pressure transmission path preferably is fluid-filled and at least reasonably well isolated from forces within the compressible wall. Two pressure measurement channels are used, one being a main channel for monitoring pressure in the pressure transmission path, and the other being a reference channel for monitoring pressure in the wall. An automatic high motion tolerance ("HMT") algorithm reduces the adverse effects of high motion artifacts from the main channel using the main channel and reference channel signals.

A caregiver applies the NIBP sensor to the patient. Immediately before the patient is about to engage in high motion activities or be placed in a high motion environment, the caregiver turns ON the automatic HMT function, and proceeds with his or her duties while observing the patient to ensure that the patient is quiet until the NIBP monitor acquires a certain number of waveforms without resetting. Once this has occurred, the caregiver may permit the high motion activity to begin.

While the automatic HMT technique may be used in any type of sensor-based noninvasive blood pressure monitor system, it is particularly useful for continuous systems such as the Vasotrac® Model APM205A NIBP monitor system. Portable sensor-based NIBP devices such as that described in U.S. patent application Ser. No. 11/072,916 filed Mar. 4, 2005 (Evans, "Sensor-based apparatus and method for portable noninvasive monitoring of blood pressure"), which herein is incorporated herein in its entirety by reference thereto, may be designed for single reading or continuous (notably short term continuous) blood pressure monitoring; where designed for continuous monitoring, a portable sensor-based NIBP device may also incorporate the automatic HMT technique.

Figure 1:
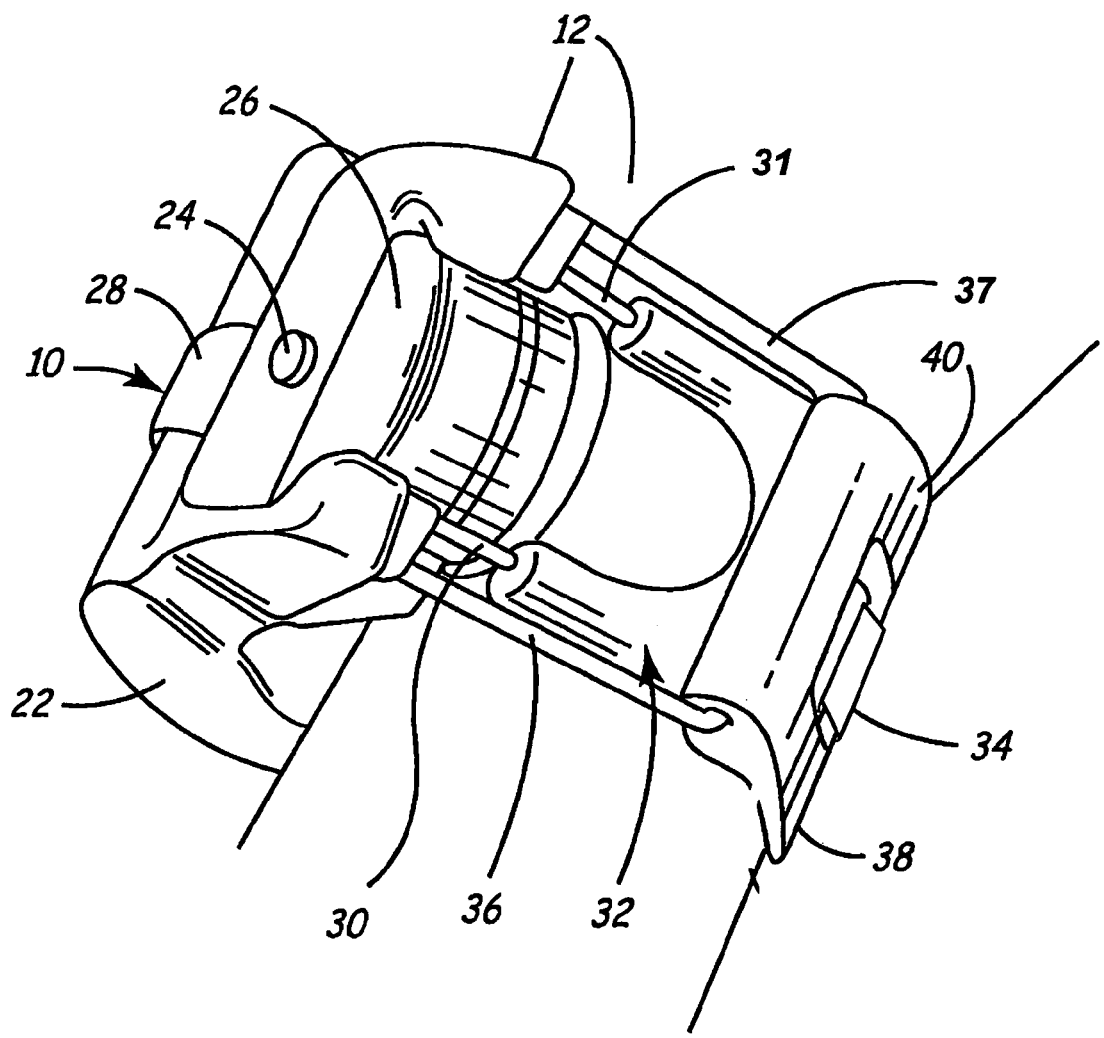
FIG. 1 is a perspective view of a noninvasive sensor assembly for a continuous noninvasive blood pressure monitoring system, wherein the sensor is shown as applied to the wrist of a patient.
Figure 2:
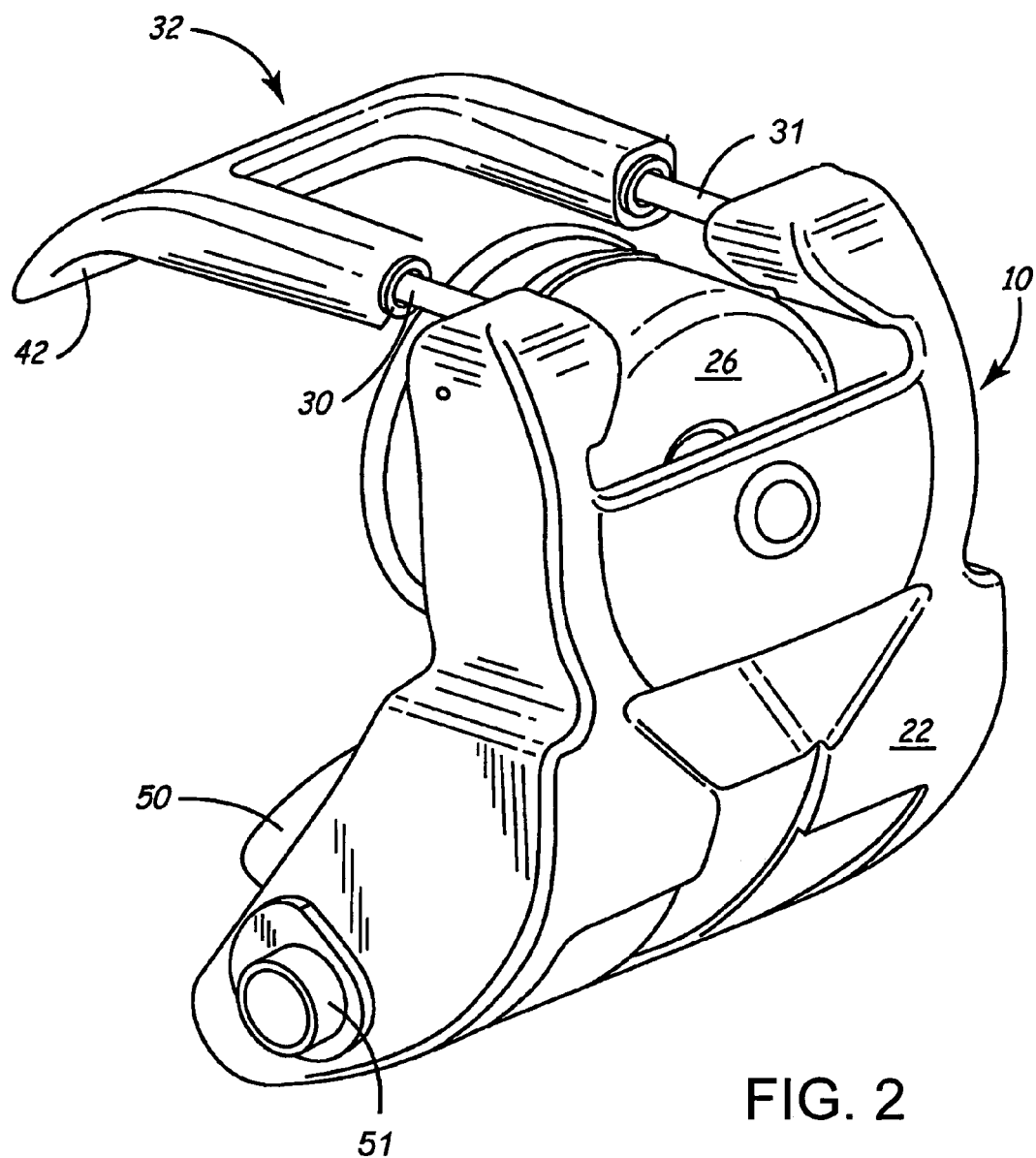
FIG. 2 is a perspective view of the sensor assembly of FIG. 1, shown without the patient's wrist and without certain holddown portions, for clarity.
Figure 3:
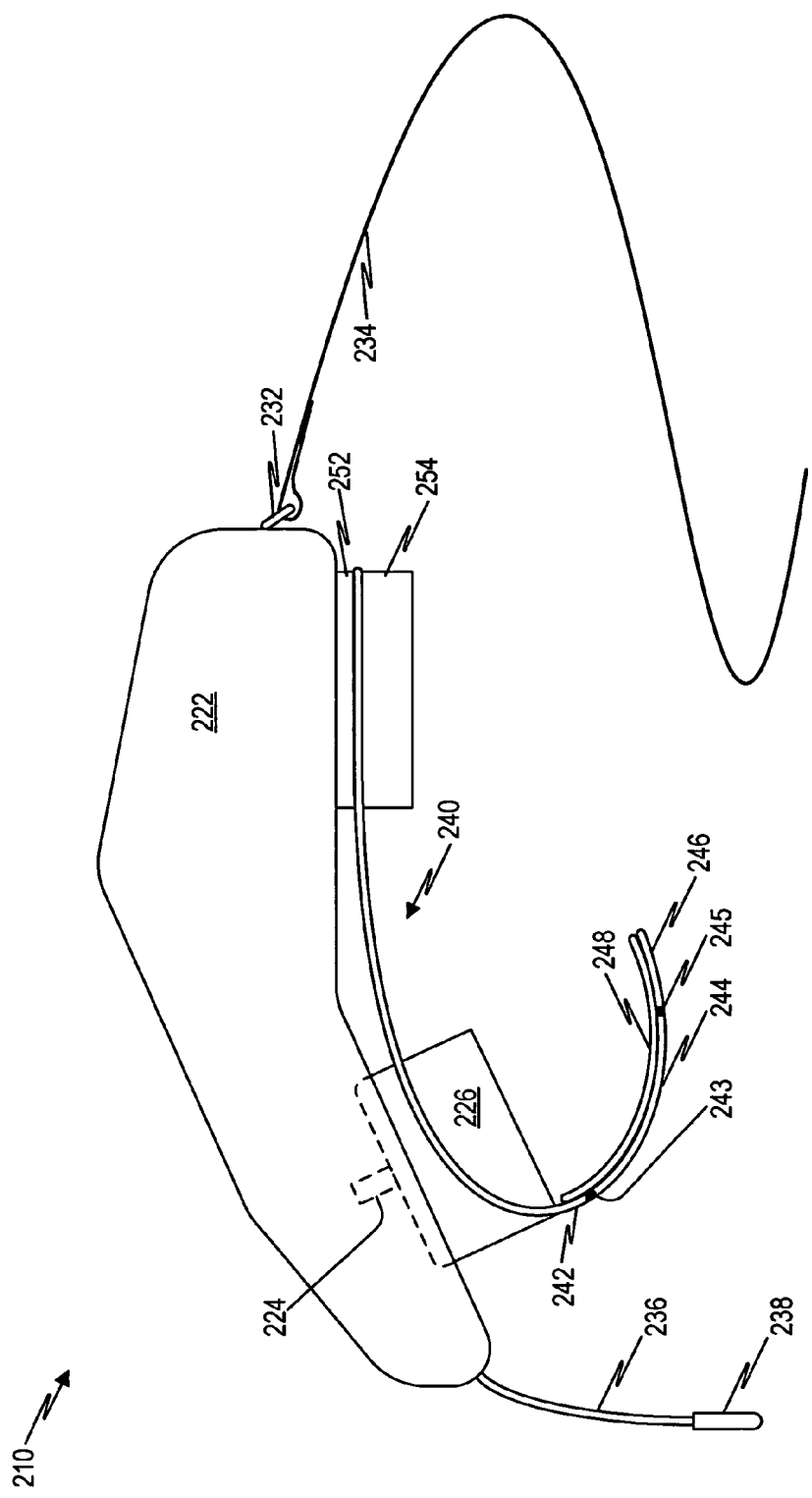
FIG. 3 is a perspective view of another noninvasive sensor assembly for a continuous noninvasive blood pressure monitoring system.

Various different types of sensor assemblies may be used. Two examples of sensor assemblies suitable for continuous monitoring are shown in FIGS. 1–3. The sensor assemblies of FIGS. 1–3 are connected to a display and control cabinet (not shown) by a cable (not shown) to form a monitoring system. Some types of monitors such as the device described in the aforementioned application Ser. No. 11/072,916 are fully self contained, insofar as the sensor assembly, display and control subsystems, and power are all integrated into a unitary device.

As shown in FIGS. 1 and 2, a sensor assembly 10 may be applied to a patient's wrist 12 to monitor blood pressure within an underlying artery of the patient. Sensor assembly 10 includes a holddown assembly 22, sensor pivot mount 24, sensor 26, and electrical flat ribbon connector 28 which electrically connects the sensor 26 and the holddown assembly 22. The holddown assembly 22 includes slide pins 30 and 31 extending from the main body of the holddown assembly 22, a locator pad 32 slidably mounted to the pins 30 and 31, a flange 38 swivel mounted on the locator pad 32, and retractable cords 36 and 37 extending from the main body of the holddown assembly 22 to the flange 38. The locator pad 42 preferably is made of flexible rubber and is curved at its end 42 to provide comfortable to patients and to better accommodate varying anatomies of patients. The flange 38 includes an opening through which a wrist strap 34 is passed to snugly secure the sensor assembly 10 around the wrist 12 so that the sensor 26 firmly contacts the wrist or, as appropriate other anatomical structure of the patient. FIG. 2 also shows that the sensor assembly 10 may include a wrist pad 50 and electrical connector 51, which is connected to the cable from the monitor cabinet (not shown).

FIG. 3 is an edge view of a sensor assembly 210 that has a housing 222 that contains a hold-down unit (not shown) which includes a pair of bale cords 236 and a bale 238. A sensor 226 is pivotally connected to the hold-down unit by a pivot rod 224. An articulated placement guide 240 is used to properly position the sensor 226 on the wrist of a patient. An illustrative articulated placement guide is described in further detail in a copending U.S. patent application Ser. No. 11/072,199 filed Mar. 4, 2005 (Kevin R. Evans, "Articulated placement guide for sensor-based noninvasive blood pressure monitor"), which hereby is incorporated herein in its entirety by reference thereto. The sensor assembly 210 is secured to the patient in any convenient manner, illustratively by strapping it on with a Velcro® brand strap 234. The ends of the strap 234 are looped through bale 238 and anchor 232, which are attached at or near opposite ends of the sensor assembly 210. The anchor 232 is illustratively a U-shaped metal bracket that rotatably projects from the housing 222. The bale 238 is a slotted plastic body which is molded about the pair of bale cords 236, and receives the end of the strap 234.

To locate the proper position for placement of the sensor 210, the user first palpates the arm with a finger to find the distal edge of the radius bone. The sensor 226 is then placed directly over this point, and the strap 234 is secured snugly. The articulated placement guide 240 that includes articulated segments 242, 244 and 246 helps in the proper placement. The placement guide is attached at one end of the segment 242 to the housing 222 by mounting block 252. When the sensor assembly 210 is applied to the patient, the placement guide 240 straddles the styloid process bone of the patient and generally guides the sensor 226 into position over the underlying artery and the radius bone. Indicator symbols such as notch symbols on the placement guide segment 244 (not shown) and an arrow symbol on the sensor 226 (not shown) align to the distal edge of the radius bone when the sensor 226 is properly positioned, and proper placement may be verified tactilely by passing a finger between the bail cords 236 and an access notch in the placement guide segments 242 and 244, and feeling the distal edge of the radius bone. The access notch extends from a generally circular aperture through which the sensor 226 moves. The portions of segment 244 that flank the aperture and access notch may be thought of as guide ribs which meet within segment 244.

When a monitoring cycle is initiated, a varying force is applied to the radial artery by the hold-down unit, and the counter pressure in the radial artery produces a signal that is digitized and used to calculate blood pressure. Measurements may be made over one or more cycles. As the hold-down unit operates, it draws in the bale 238 via the bale cords 236, so that sensor 226 gently exerts pressure against the patient's wrist over the radial artery, while cushion 254 on the placement guide segment 242 and layer 248 extending across whole or parts of placement guide segments 242, 244 and 246 and spanning intervening gaps 243 and 245 gently distribute pressure over other areas of the patient's wrist. The cushion 254 also functions as a pivot point about which the hold-down pressure is applied, while the layer 248 also enables articulation.

In both versions, the holddown assemblies 22 and 222 force the sensors 26 and 226 against the wrist by retraction of the cords 36 and 37 and the cord pair 236. The holddown assemblies 22 and 222 control the rate and amount of retraction of the cords 36 and 37 and the cord pair 236, and thus controls the amount and rate of the varying pressure.

Generally, a varying pressure, and more preferably a sweeping pressure, is applied to the wrist or other anatomical structure. The sensors 26 and 226 both include two pressure transducers, a main pressure transducer for the main channel, and a reference pressure transducer for the reference channel.

Figure 4:
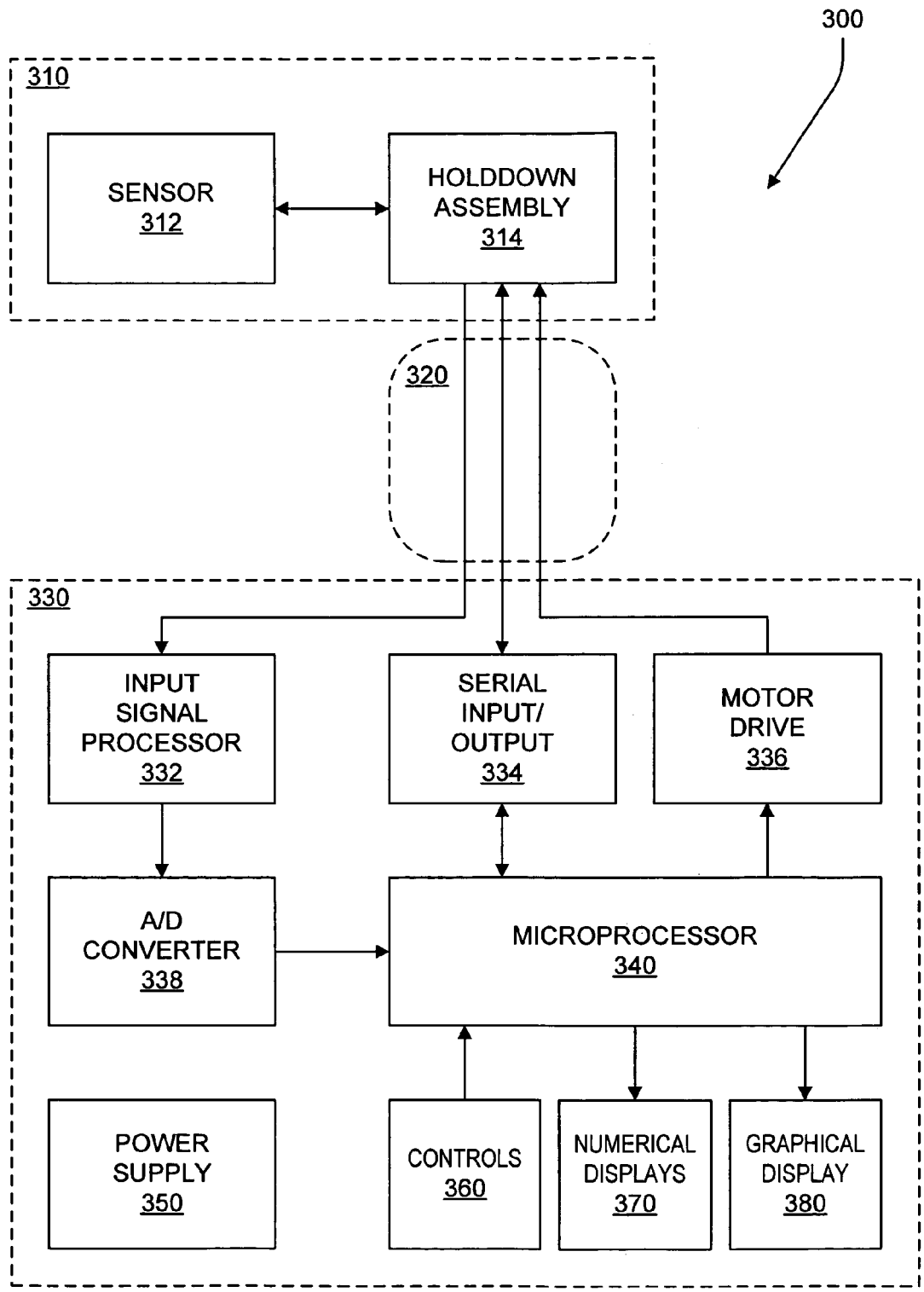
FIG. 4 is a schematic functional block diagram of a continuous noninvasive blood pressure monitoring system.

FIG. 4 is a schematic block diagram of a continuous noninvasive blood pressure monitoring system 300, which includes a sensor assembly 310 and a control and display system 330, connected by a cable 320. The sensor assembly 310 includes sensor 312 and holddown assembly 314. The control and display system 330 includes a microprocessor 340. Input signal processor 332 and analog-to-digital converter 338 furnish digitized main and reference channel signals to an input of the microprocessor 340. Control and status signals between the sensor assembly 310 and the microprocessor 340 pass through serial input/output circuit 334. The motor in the holddown assembly 314 is controlled by the microprocessor 340 through a motor drive circuit 336. User control of the microprocessor 340 is done through various controls 360, which may include a keyboard, switches, soft switches, selector knobs, and so forth by which the system may be tested, calibrated, and operated in various modes. Information is displayed to the user through various numerical displays 370 and a graphical display 380. A power supply 350 is also provided.

The microprocessor 340 along with associated memory (not shown) controls the motor drive 336 to vary the applied holddown pressure, calculates systolic, diastolic, and mean pressure and pulse from the data from the sensor 312, and executes an automatic high motion tolerance algorithm when activated.

The high motion tolerance ("HMT") algorithm cancel high motion artifacts from the main channel using the main channel and reference channel signals. The main channel is sensitive to pressure produced by the artery and by high motion conditions, as well as, to some extent, pressure produced by the holddown force. The pressure in the main channel may be represented as:

$$P_{MC} = P_A + P_{HM} + P_{HF1} \quad (1)$$

The reference channel is sensitive to pressure produced by the high motion conditions and by the holddown force, but is not significantly sensitive to pressure produced by the artery. The pressure in the reference channel may be represented as:

$$P_{RC} = P_{HM} + P_{HF2} \quad (2)$$

The data obtained from the main channel and the reference channel is filtered though respective high pass filters, resulting in removal of $P_{HF1}$ and $P_{HF2}$ from the main and reference signals respectively, and resulting in the following signals:

$$P_{MC} = P_A + P_{HM} \quad (3)$$

$$P_{RC} = P_{HM} \quad (4)$$

The filtered main and reference signals are then processed by two stages of adaptive filters. The first stage switches between two models of non-linear least means square ("NLMS") adaptive noise cancellers. The two models work on the up and down part of the sweep respectively. The second stage is an adaptive linear predictor (IIR model) and works on the main signal alone. In effect, the result achieved by the two stages may be expressed as follows:

$$P_{MC} - P_{RC} = P_A \quad (5)$$

The adaptive linear predictor automatically identifies a predetermined number of valid sweeps using predetermined criteria indicative of low motion conditions, and uses these sweeps as a baseline for adjusting subsequent sweeps for possible high motion conditions.

Since the sensor 312 is relatively small compared to the larger cuffs used with oscillometric and auscultatory methods, the sensor 312 exerts pressure to only a relatively small area above the underlying artery of the patient. Consequently, blood pressure measurements may be taken with less discomfort to the patient. Because the sensor 312 does not require inflation or deflation, faster and more frequent measurements may be taken. Furthermore, the sensor 312 conforms well to the anatomy of the patient.

Figure 5:
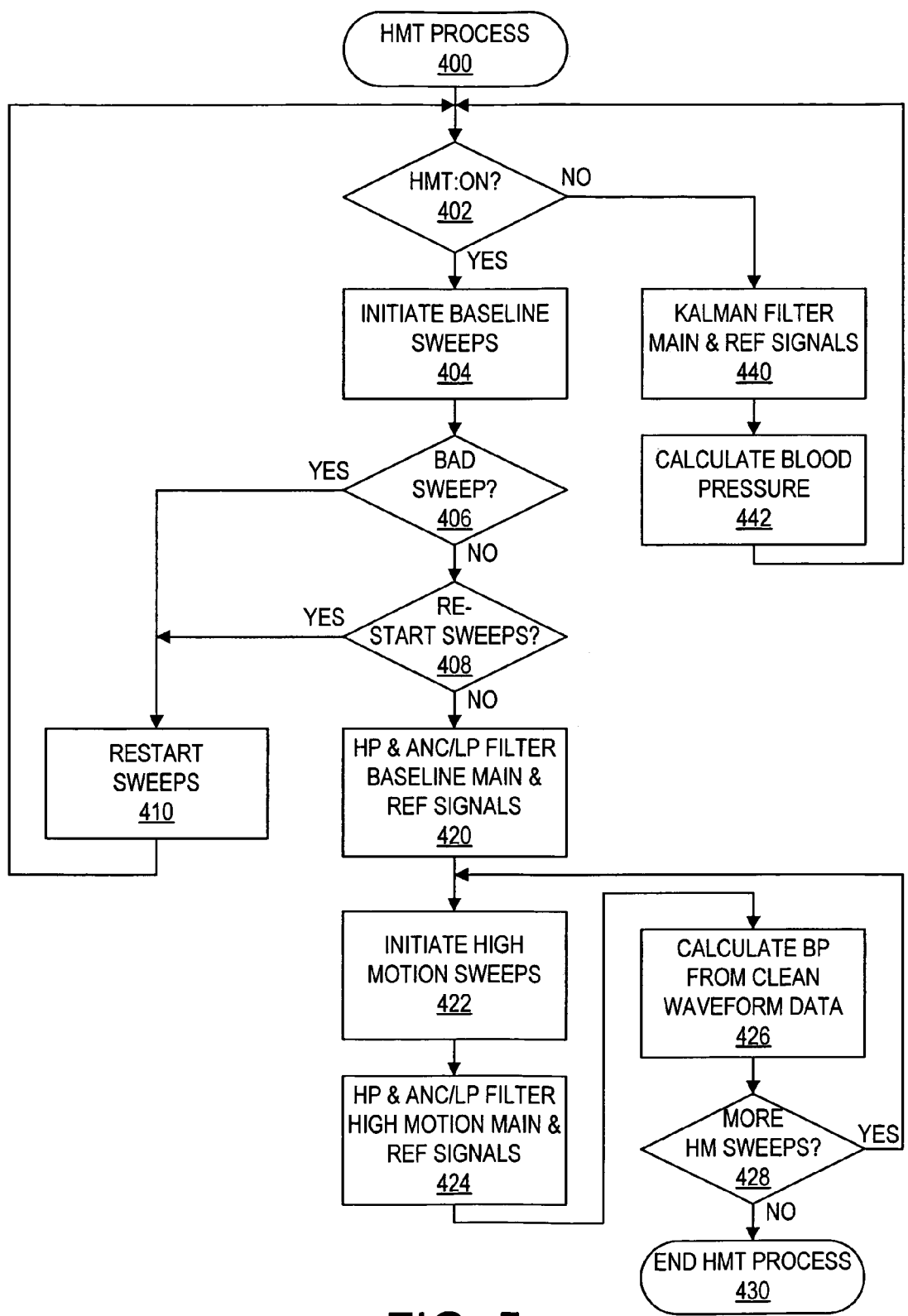
FIG. 5 is a flowchart of an automated high motion tolerance algorithm for a continuous noninvasive blood pressure monitoring system such as shown in FIG. 4.

FIG. 5 is a flowchart of an automated high motion tolerance algorithm 400 for a continuous noninvasive blood pressure monitoring system such as shown in FIG. 4. The algorithm 400 proceeds by determining whether HMT has been switched on (block 402). If not, processing proceeds by filtering the main and reference channel waveform data with a Kalman filter (block 440) and then by calculating blood pressure (block 442). However, if HMT:ON is detected, a number of baseline sweeps are initiated (block 404). Although preferably only the last sweep is used for the baseline, having a number of sweeps such as four or five allows the patient to settle down and allows the caregiver to make a good observation of the patient's degree of motion.

The algorithm checks whether any of the baseline sweeps is a bad sweep (block 406), which is likely to occur if the patient jerks or if the sensor is not accurately placed. A bad sweep may be indicated by any of the following illustrative occurrences: (1) a safety limit holddown pressure in excess of 280 mmHg; (2) a calculated systolic rate value in excess of 600 mmHg; (3) a calculated diastolic rate value in excess of 600 mmHg; (4) a calculated mean rate value in excess of 600 mmHg; (5) a calculated systolic rate value that is not greater than the calculated diastolic rate value; (6) a calculated systolic rate value that is not greater than the calculated mean value; (7) a calculated diastolic rate value that is not less than the calculated systolic rate value and the calculated mean value; (8) a calculated diastolic rate value that is zero or less; (9) a calculated mean value that is less than the calculated diastolic rate value; and (10) a calculated mean value that is less than the calculated systolic rate value.

The algorithm also checks whether the caregiver or patient wishes to restart the baseline sweeps (block 408) because of observed motion that may not have been serious enough to generate a bad sweep but which may have caused an unreliable sweep.

If a problem occurs, the algorithm is restarted to begin a new set of baseline sweeps (block 410) and the process resumes with block 402. An illustrative convenient way to restart the sweeps is for the caregiver or patient to press the following sequence of keys: HMT:OFF, HMT:ON, HMT: AUTO.

If no problem occurs, the ANC/LP algorithm is referenced on preferably the last baseline sweep (block 420), the high motion sweeps are initiated (block 422), clean waveform data are obtained by applying high pass filtering and the ANC/LP algorithm to the main and reference signals (block 424), and blood pressure is calculated in any suitable manner from the clean waveform data (block 426). If additional HMT sweeps are desired, the process resumes with block 422 (block 428—yes). If monitoring is completed or if the blood pressure readings or waveforms as observed appear to be of low confidence, the HMT process is terminated (block 430), although it may be restarted with block 400.

Once a clean main signal is obtained, blood pressure values such as systolic blood pressure, diastolic blood pressure, mean blood pressure, and pulse rate may be calculated in any desired manner. One suitable manner calculates the blood pressure values with functions that use parameters derived from the waveform data of the clean main channel signal and coefficients obtained from clinical tests upon patients having known blood pressure values. A suitable basic algorithm is described in U.S. Pat. No. 5,797,850 issued Aug. 25, 1998 to Archibald et al., which is incorporated herein in its entirety by reference thereto. Enhancements to the basic algorithm include a beat onset detection method as described in U.S. Pat. No. 5,720,292 issued Feb. 24, 1998 to Poliac, and a segmentation estimation method as described in U.S. Pat. No. 5,738,103 issued Apr. 14, 1998 to Poliac, which also are incorporated herein in their entirety by reference thereto.

Figure 6:
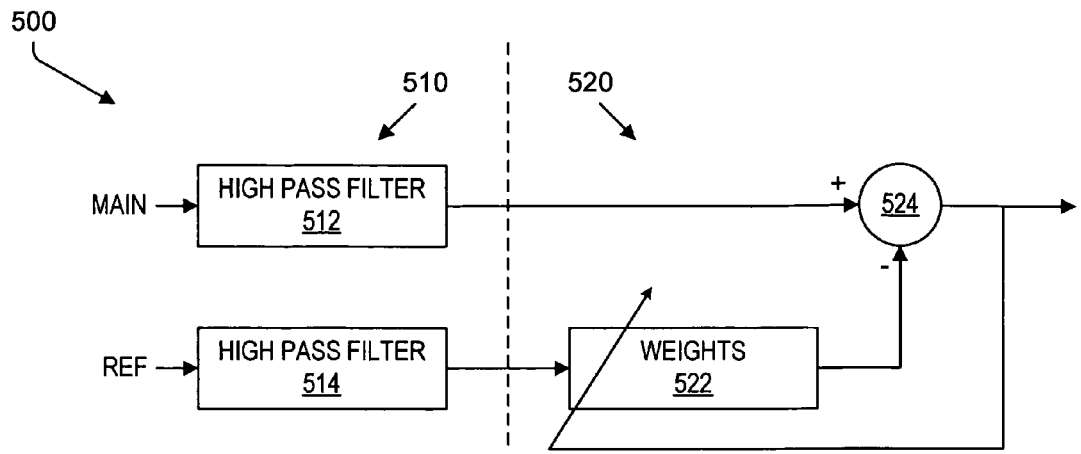
FIG. 6 is a schematic block diagram of a filter architecture suitable for the high motion tolerance algorithm of FIG. 9.

FIG. 6 is a schematic block diagram of a filter architecture suitable for the high motion tolerance algorithm of FIG. 5. The architecture includes two stages, a high pass filter stage 510 and a second adaptive filter stage 520. The high pass filters 512 and 514 pass data at frequencies likely to contain meaningful pressure data. The filtered main and reference signals then are applied to the adaptive filter stage 520. The adaptive filter stage 520 includes an adaptive noise canceller having weights 522 and a summation element 524. The reference channel signal is applied to the weights 522, which makes it more similar to that of the main transducer. The adaptive noise canceller preferably incorporates a normalized least mean square (NLMS) algorithm. The weighted reference channel signal is subtracted from the main channel signal in the summation element 524 to produce a so-called "error" signal (as it is termed in the art), which is the corrected pressure data.

Figure 7:
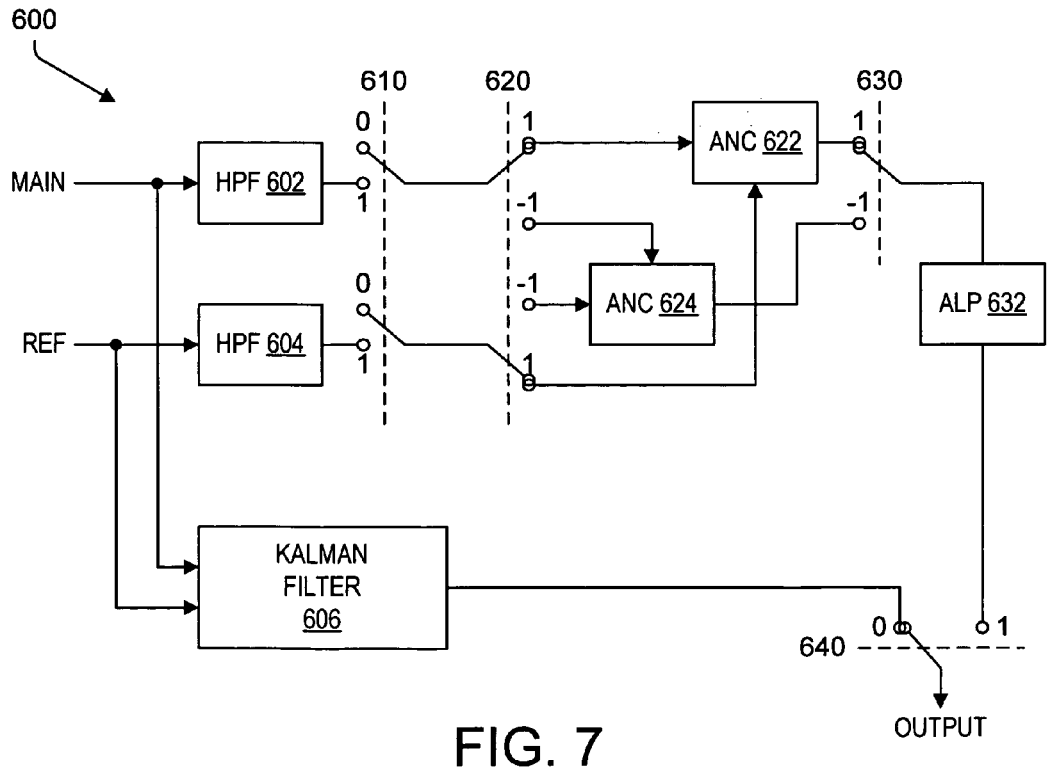
FIG. 7 is a state diagram for the filter shown in FIG. 10.

The second filter stage 520 may also include an adaptive linear predictor (see FIG. 7). An adaptive linear predictor tailors a prediction function to the reference channel signal by minimizing its prediction error according to desired criterion. Thus, the adaptive linear predictor receives as its input signals the sample signal retrieved from the patient in a low motion environment and the signal received from the adaptive noise canceller. The output of the adaptive linear predictor is waveform data that is tailored to the characteristics of the reference signal. Preferably, the adaptive linear predictor uses an infinite impulse response ("IIR") model as its prediction function.

Figure 10:
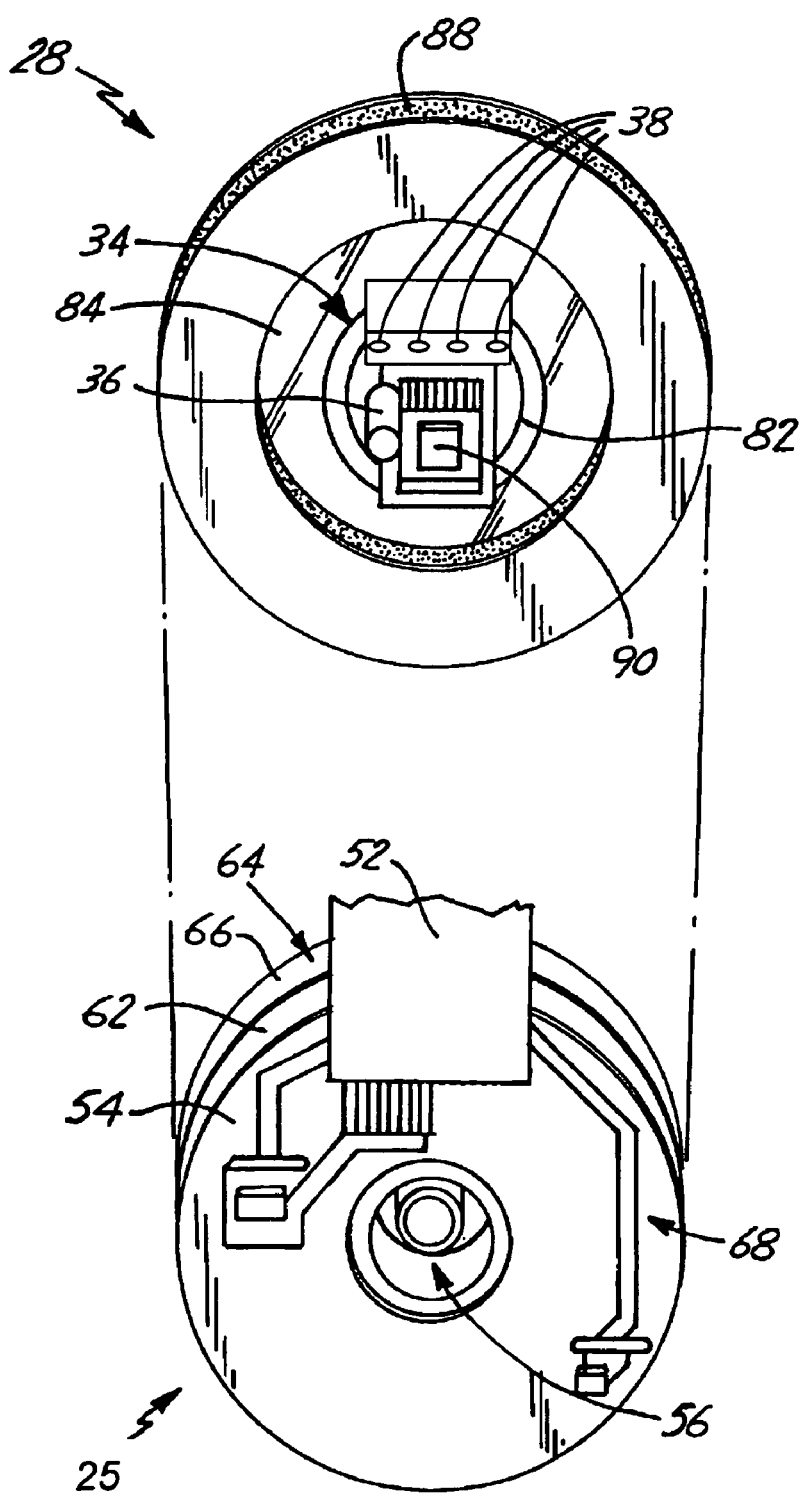
FIG. 10 is a top exploded view of the base section and the sensing section shown in FIGS. 8A–8C and in FIGS. 9A–9C.

FIG. 7 is a state diagram 600 for the filter shown in FIG. 10. Two states are shown, a filter state represented by ganged switches 610 and 640, and a sweep state represented by ganged switches 620 and 630. The filter state may be either "0" for HTM:OFF in which the noise is less than a predetermined threshold, or "1" for HMT:ON in which the noise is greater than a predetermined threshold. The sweep state may be either "1" for an up-sweep, or "−1" for a down sweep. When HMT is off, the filter state switches 610 and 640 are in the "0" position as shown. The main channel signal and the reference channel signal are furnished to a Kalman filter 606 to eliminate such low level incidental noise as may occur. The Kalman filter is a well-known recursive technique to estimate the state of a process, in a way that minimizes the mean of the squared error. The output of the Kalman filter is selected by the switch 640 and supplied as the output of the filter 600. The sweep state is irrelevant. When HMT is on, the filter state switches 610 and 640 are in the "1" position. During an up-sweep, the sweep state switches 620 and 630 are in the "1" position as shown, and the main channel and the reference channel signals are filtered by respective high pass filters 602 and 604 and are applied to up-sweep adaptive noise canceller component 622. The output of the up-sweep adaptive noise canceller component 622 is selected by switch 630 and applied to an adaptive linear predictor 632. The output of the adaptive linear predictor 632 is selected by switch 640 and supplied as the output of the filter 600. During a down-sweep, the sweep state switches 620 and 630 are in the "−1" position, and the main channel and the reference channel signals are filtered by respective high pass filters 602 and 604 and applied to down-sweep adaptive noise canceller component 624. The output of the down-sweep adaptive noise canceller component 624 is selected by the switch 630 and applied to the adaptive linear predictor 632. The output of the adaptive linear predictor 632 is selected by switch 640 and supplied as the output of the filter 600.

The HMT algorithm may be used with a variety of sensor designs. An illustrative one-part unitary sensor design is described in the aforementioned '022 patent.

Figure 8A:
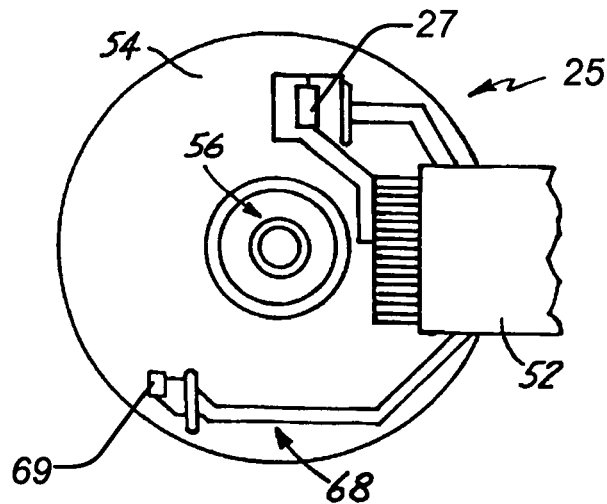
FIG. 8A is a top view of a base section of a sensor suitable for use in the sensor assemblies shown in FIGS. 1–3.
Figure 8B:
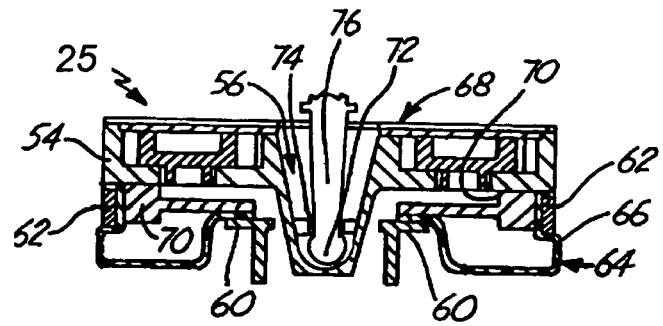
FIG. 8B is a sectional view of the base section of FIG. 4A.
Figure 8C:
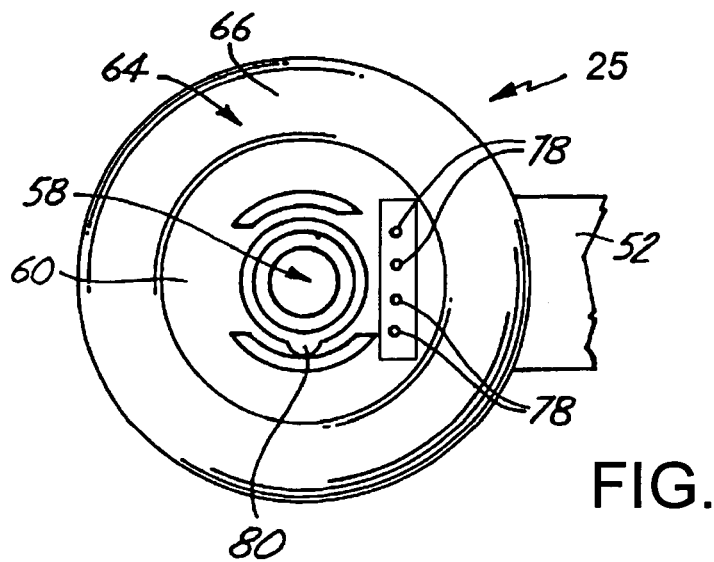
FIG. 8C is a bottom view of the base section of FIG. 4A.

An illustrative two-part unitary sensor design in which the part of the sensor that contacts the patient is replaceable is shown in FIGS. 8A–8C, 9A–9C, 10 and 11. FIGS. 8A–8C show top, sectional, and bottom views, respectively, of a base section 25 of the two-part sensor. Base section 25 includes a top plate 54, an upper receptacle 56, a lower receptacle 58, an inner mounting ring 60, an outer mounting ring 62, and a flexible ring 64. The flexible ring 64 is defined by side wall diaphragm 66 and upper capture 70. The outer edge portion of diaphragm 66 is held between top plate 54, outer ring 62 and upper capture 70, while the inner edge portion of diaphragm 66 is held between inner ring 60 and upper capture 70. The flexible ring 64 is filled with fluid, and is deformable in the vertical direction so as to be able to conform to the contour of the anatomy of the patient surrounding the underlying artery. Because fluid is permitted to flow through and around ring 64, pressure is equalized around the patient's anatomy.

The base section 25 also includes a pivot mount 72 for pivotally joining the sensor to a pivot post (not shown) that extends from the hold-down assembly. The pivot mount 72 allows the sensor to pivot near the wrist surface to accommodate a range of patient anatomies.

The base section 25 receives a sensing section 28 (FIGS. 9A–9C), and includes electrical connectors 78 and an alignment receptacle 80 in, illustratively, the inner mounting ring 60 of the lower receptacle 58, for receiving a mating connector 34 (FIGS. 9A & 10) in the sensing section 28. The sensing section 28 may be permanently joined or detachably joined to the base section 25.

The base section 25 also includes a reference channel pressure transducer 27, an electrical circuit 68 that includes a memory chip 69, and an electrical connector 52, illustratively a ribbon cable, for power and communication of pressure signals from transducers 27 and 90 (FIG. 9A) in the sensor and for communication of data to and from the memory chip 69. Power and communication with the transducer 90 is through the connectors 78.

Figure 9A:
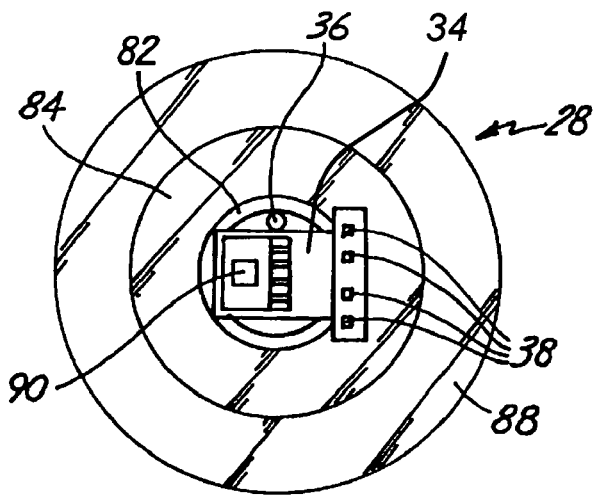
FIG. 9A is a top view of a sensing section of a sensor suitable for use in the sensor assemblies shown in FIGS. 1–3.
Figure 9B:
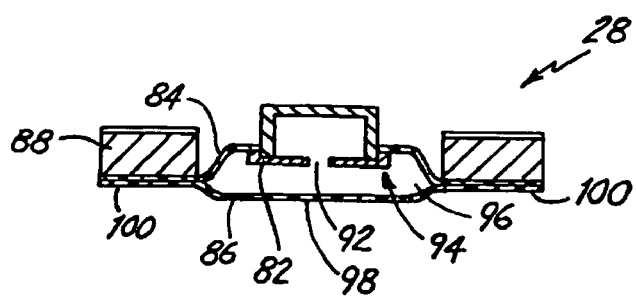
FIG. 9B is a sectional view of the sensing section of FIG. 5A.
Figure 9C:
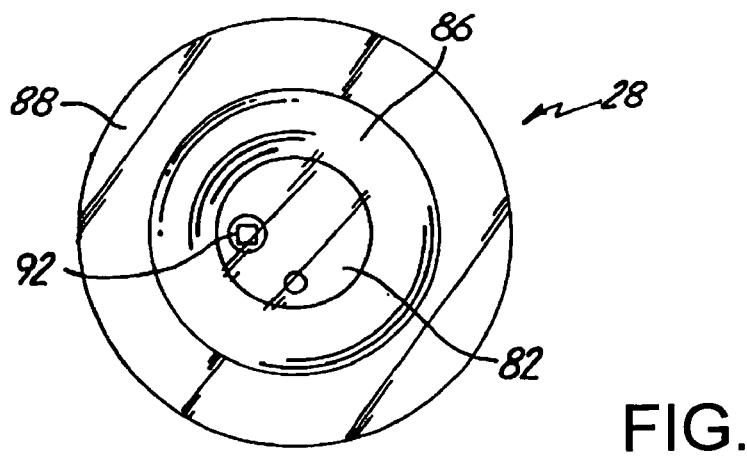
FIG. 9C is a bottom view of the sensing section of FIG. 5A.

FIGS. 9A–9C show top view, sectional and bottom views, respectively, of sensing section 28 of the sensor. Sensing section 28 includes a diaphragm capture 82, an inner diaphragm 84, a flexible (or outer) diaphragm 86, a compressible ring 88, a main channel pressure transducer 90 having a sensing surface 92, and connector 34. Inner diaphragm 84 and flexible diaphragm 86 form a sensor chamber 94 which is filled with preferably a fluid coupling medium 96.

Any of a variety of different types of pressure transducers may be used for the main channel transducer 90 and the reference channel transducer 27, one suitable type being part number MPX2300DT1 or MPX2301DT1, which is available from Freescale Semiconductor, Inc. of Austin, Tex., and from Motorola Inc. of Tempe, Ariz.

The connector 34 illustratively includes an alignment element 36 and electrical connectors 38. Electrical connectors 38 are connected to and extend from pressure transducer 90. Electrical connectors 38 mate with electrical connectors 78 located on the base section 26. Electrical connectors 38 provide the connection between transducer 90 and the electrical circuitry of the base section 26. Alignment element 36 is received by alignment receptacle 80 (FIG. 8C) of base section 25 to precisely position electrical connectors 38 within the corresponding electrical connectors 78 of the base section 25. It will be appreciated that any suitable mating electrical connectors may be used for the electrical connectors 38 and 78; illustratively, electrical connectors 38 are receptacles or sockets, while electrical connectors 78 are recessed pins.

Compressible ring 88 is generally annular and may be formed from a polyurethane foam or other compressible material that also has pressure pulse dampening properties, including open cell foam and closed cell foam. Ring 88 is centered about flexible diaphragm 86 and positioned above diaphragms 84 and 86. Compressible ring 88 is isolated from the fluid coupling medium 96 within sensor chamber 94. The compressibility of ring 88 allows ring 88 to absorb and dampen forces in a direction parallel to the underlying artery. These forces are exerted by the blood pressure pulses on sensing section 28 as the blood pressure pulses cross flexible diaphragm 86. Because compressible ring 88 is reasonably well isolated from fluid coupling medium 96, the forces absorbed or received by ring 88 are not well transmitted to fluid coupling medium 96. Instead, these forces are transmitted across compressible ring 88 and flexible ring 64 to top plate 54 (shown in FIG. 4B), which is a path distinct and separate from fluid coupling medium 96.

Rings 64 and 88 apply force to the anatomy of the patient to neutralize the forces exerted by tissue surrounding the underlying artery. Rings 64 and 88 are compressible in height, thus the height of the side of the sensor 20 decreases as the sensor 20 is pressed against the patient's wrist.

Inner diaphragm 84 is an annular sheet of flexible material having an inner diameter sized to fit around diaphragm capture 82. An inner portion of inner diaphragm 84 is trapped or captured, and may be adhesively affixed to the lip of diaphragm capture 82. Inner diaphragm 84 is permitted to initially move upward as flexible diaphragm 86 conforms to the anatomy of the patient surrounding the underlying artery. As compressible ring 88 is pressed against the anatomy of the patient surrounding the artery to neutralize or offset forces exerted by the tissue, flexible diaphragm 86 is also pressed against the anatomy and the artery. However, because inner diaphragm 84 is permitted to roll upward, sensor chamber 94 does not experience a large volume decrease or a large corresponding pressure increase. Thus, greater force is applied to the anatomy of the patient through compressible ring 88 to neutralize tissue surrounding the artery without causing a corresponding large, error-producing change in pressure within sensor chamber 94 as the height of the side wall changes and the shape of flexible diaphragm 86 changes. As a result, the sensor 20 achieves more consistent and accurate blood pressure measurements.

Flexible diaphragm 86 is a generally circular sheet of flexible material capable of transmitting forces from an outer surface to fluid coupling medium 96 within sensor chamber 94. Diaphragm 86 is coupled to inner diaphragm 84 and is configured for being positioned over the anatomy of the patient above the underlying artery. Diaphragm 86 includes an active portion 98 and a nonactive portion 100 or skirt. Non-active portion 100 constitutes the area of diaphragm 86 where inner diaphragm 84 is heat sealed or bonded to diaphragm 86 adjacent compressible ring 88. Active portion 98 of flexible diaphragm 86 is not bonded to inner diaphragm 84, and is positioned below and within the inner diameter of ring 88. Active portion 98 of diaphragm 86 is the active area of sensing section 28 which receives and transmits pulse pressure to pressure transducer 90.

Fluid coupling medium 96 within sensor chamber 94 may be any fluid (gas or liquid) capable of transmitting pressure from flexible diaphragm 86 to transducer 90. Alternatively, another pressure pulse transmission medium may be used, including a medium made of a solid material or materials, or combinations of different materials, solid and fluid. Fluid coupling medium 96 interfaces between active portion 98 of diaphragm 86 and transducer 90 to transmit blood pressure pulses to transducer 90. Because fluid coupling medium 96 is contained within sensor chamber 94, which is isolated from compressible ring 88 of sensing section 28, fluid coupling medium 96 does not transmit blood pressure pulses parallel to the underlying artery, forces from the tissue surrounding the underlying artery, and other forces absorbed by compressible ring 88 to transducer 90. As a result, sensing section 28 more accurately measures and detects arterial blood pressure.

Sensing section 28 permits accurate and consistent calculation of blood pressure. Although blood pressure pulses are transmitted to the transducer 90 through hole 92, sensing section 28 is not dependent upon precisely accurate positioning of the sensor over the underlying artery because of the large sensing surface of the active portion 98 of the flexible diaphragm 86. Thus, the sensor is tolerant to some sensor movement as measurements are being taken.

Figure 11:
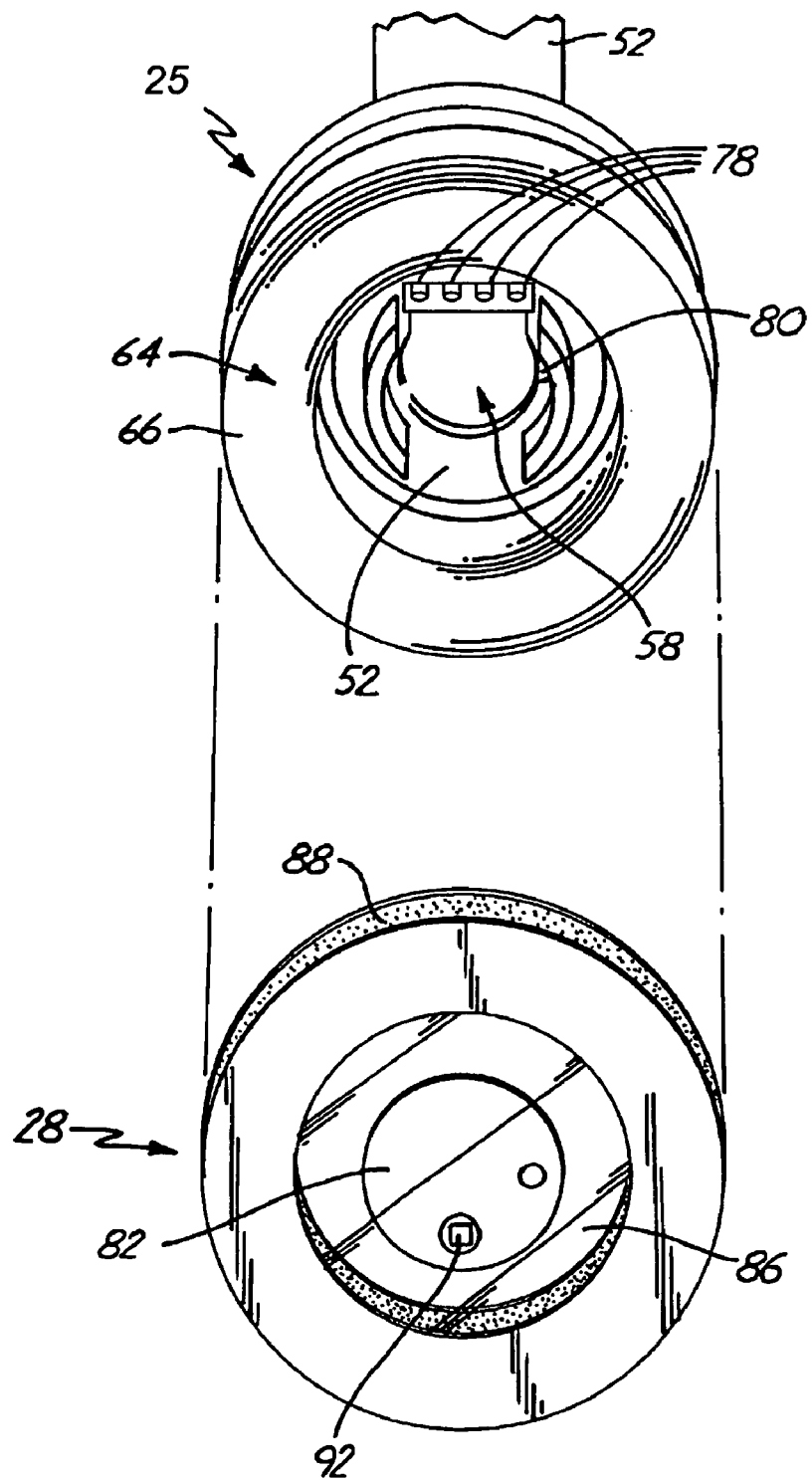
FIG. 11 is a bottom exploded view of the base section and the sensing section shown in FIGS. 8A–8C and in FIGS. 9A–9C.

FIG. 10 is a top exploded view of the base section 25 and the sensing section 28 and FIG. 11 is a bottom exploded view of the base section 25 and the sensing section 28. When assembled, flexible ring 64 and compressible ring 88 form the side wall of the sensor 20. The connector 34 of sensing section 28 may be used to detachably connect sensing section 28 to base section 25.

The sensor achieves a zero pressure gradient across active portion 98 of the sensing section 28, achieves a zero pressure gradient between transducer 90 and the underlying artery, attenuates or dampens pressure pulses that are parallel to sensing surface 92 of transducer 90, and neutralizes forces of the tissue surrounding the underlying artery. The sensor contacts and applies force to the anatomy of the patient across non-active portion 100 and active portion 98 of flexible diaphragm 86. However, the pressure within sensor chamber 94 is substantially equal to the pressure applied across active portion 98 of flexible diaphragm 86. In addition, because fluid coupling medium 96 within sensor chamber 94 is isolated from ring 88, pressure pulses parallel to the underlying artery, forces from tissue surrounding the underlying artery, and other forces absorbed by ring 88 are not transmitted through fluid coupling medium 96 to transducer 90. Consequently, the sensor also achieves a zero pressure gradient between transducer 90 and the underlying artery.

The remaining force applied by the sensor across non-active portion 100, which neutralizes or offsets forces exerted by the tissue surrounding the underlying artery, is transferred through the side wall (rings 64 and 88) to top plate 54. As a result, the geometry and construction of the sensor provides a suitable ratio of pressures between non-active portion 100 and active portion 98 of flexible diaphragm 86 to neutralize tissue surrounding the underlying artery and to accurately measure the blood pressure of the artery.

If desired, sensing section 28 may be made detachably connected to base section 25 such that sensing section 28 may be replaced if contaminated or damaged, or if it is desired to use a new disposable contact element with each new patient. Although the sensor is described as having a distinct base section 26 and a distinct sensing section 28 which includes the pressure transducer 90, the sensor need not comprise distinct base and sensing sections. Although the sensor is described as a unitary structure in which the pressure transducer 90 is mounted to the sensing section 28, various components of the sensor such as the pressure transducer 90 may be distributed. As an example, the pressure transducer may be mounted to a different structure away from the base, and placed in fluid communication with the sensing surface through a fluid-filled tube.

It will therefore be appreciated that the description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A method for monitoring blood pressure of a patient under high motion conditions, comprising:
   securing a sensor assembly to a monitoring site on an anatomical structure of the patient from which noninvasive monitoring of blood pressure may be performed, the sensor assembly having a sensor with a main pressure channel and a reference pressure channel;
   applying the sensor to the monitoring site with a varying holddown force over a plurality of sequential cycles comprising an initial sequence of a predetermined number of cycles and a subsequent sequence;
   attempting to maintain low motion conditions over the initial sequence of the applying step;
   acquiring main waveform data from the main pressure channel and reference waveform data from the reference pressure channel during the applying step;
   monitoring at least one of the main waveform data and the reference waveform data to detect a fault in the initial sequence of the applying step;
   monitoring a user-activated restart control to detect a restart signal during the initial sequence of the applying step; and
   when no fault is detected in the waveform data monitoring step, and when no restart signal is detected in the reset control monitoring step, calculating blood pressure from the main and reference waveform data acquired in the subsequent sequence of the applying step and from at least one cycle of the initial sequence after filtration thereof with respective high pass filters, an adaptive noise canceller, and an adaptive linear predictor.

2. The method of claim 1 wherein:
   the sensor assembly securing step comprises securing the sensor assembly to a wrist of the patient with the sensor aligned to a distal edge of a radius bone of the wrist and over an artery;
   activating the user-activated restart control when the wrist of the patient is observed to undergo motion; and
   restarting the acquiring step.

3. The method of claim 1 further comprising:
   detecting a fault when (1) a safety limit holddown pressure exceeds 280 mmHg; (2) a calculated systolic rate value exceeds 600 mmHg; (3) a calculated diastolic rate value exceeds 600 mmHg; (4) a calculated mean rate value exceeds 600 mmHg; (5) a calculated systolic rate value is not greater than a calculated diastolic rate value; (6) a calculated systolic rate value is not greater than a calculated mean value; (7) a calculated diastolic rate value is not less than a calculated systolic rate value and a calculated mean value; (8) a calculated diastolic rate value is zero or less; (9) a calculated mean value is less than a calculated diastolic rate value; or (10) a calculated mean value is less than a calculated systolic rate value; and
   restarting the acquiring step.

4. The method of claim 1 wherein:
   the sensor assembly securing step comprises securing the sensor assembly to a wrist of the patient with the sensor aligned to a distal edge of a radius bone of the wrist and over an artery;
   activating the user-activated restart control when the wrist of the patient is observed to undergo motion;
   detecting a fault when (1) a safety limit holddown pressure exceeds 280 mmHg; (2) a calculated systolic rate value exceeds 600 mmHg; (3) a calculated diastolic rate value exceeds 600 mmHg; (4) a calculated: mean rate value exceeds 600 mmHg; (5) a calculated systolic rate value is not greater than a calculated diastolic rate value; (6) a calculated systolic rate value is not greater than a calculated mean value; (7) a calculated diastolic rate value is not less than a calculated systolic rate value and a calculated mean value; (8) a calculated diastolic rate value is zero or less; (9) a calculated mean value is less than a calculated diastolic rate value; or (10) a calculated mean value is less than a calculated systolic rate value; and
   restarting the acquiring step upon occurrence of either the user-activated restart control activating step or the fault detecting step.

* * * * *